United States Patent
Rudzinski et al.

(10) Patent No.: US 8,001,961 B2
(45) Date of Patent: Aug. 23, 2011

(54) CONTAINER FOR INHALATION ANESTHETIC

(75) Inventors: Ralph V. Rudzinski, Martinsville, NJ (US); Ralph A. Lessor, New Providence, NJ (US)

(73) Assignee: Baxter International Inc., Deerfield, IL (US)

( * ) Notice: Subject to any disclaimer, the term of this patent is extended or adjusted under 35 U.S.C. 154(b) by 2222 days.

(21) Appl. No.: 09/952,039

(22) Filed: Sep. 13, 2001

(65) Prior Publication Data

US 2002/0068767 A1 Jun. 6, 2002

Related U.S. Application Data

(60) Provisional application No. 60/233,302, filed on Sep. 15, 2000.

(51) Int. Cl.
*A61M 11/00* (2006.01)
*A61K 9/12* (2006.01)
*A61K 9/14* (2006.01)

(52) U.S. Cl. ............ 128/200.14; 128/200.23; 424/45; 424/46; 514/958

(58) Field of Classification Search ............ 424/45, 424/400, 451, 46; 128/200.14, 200.23; 514/958
See application file for complete search history.

(56) References Cited

U.S. PATENT DOCUMENTS

| | | | |
|---|---|---|---|
| 2,720,203 A | 10/1955 | Burns et al. | |
| 4,250,334 A | 2/1981 | Coon et al. | |
| 5,505,236 A | 4/1996 | Grabenkort et al. | |
| 5,617,906 A | 4/1997 | Braatz et al. | |
| 5,679,576 A | 10/1997 | Kawai et al. | |
| 5,990,176 A | 11/1999 | Bieniarz et al. | |
| 6,008,273 A | 12/1999 | Leibelt et al. | |
| 6,074,668 A | 6/2000 | Flament-Garcia et al. | |
| 6,083,514 A | 7/2000 | Chang et al. | |
| 6,162,443 A | 12/2000 | Flament-Garcia et al. | |
| 6,253,762 B1 * | 7/2001 | Britto ...................... | 128/200.14 |
| 6,315,985 B1 * | 11/2001 | Wu et al. ........................ | 424/45 |
| 2001/0000729 A1 | 5/2001 | Flament-Garcia et al. | |

FOREIGN PATENT DOCUMENTS

EP 0 642 992 A2 3/1995
WO WO 99/34762 7/1999

OTHER PUBLICATIONS

Product Data Sheet for HOBA Internal Lining for Aerosol Cans: 7407P; Jan. 1995; 1 page.
Safety Data Sheet for HOBOA Lining: 7407P; Jan. 1986; 1 page.
Correspondence between Monobloc USA and HOBA Industrie-Chemie GmbH re: 7407P with product sheets; Dec. 17, 1986 and Jan. 20, 1987; 4 pages.
Examination Report of Professor Dr. Peter Nehring re: HOBA 7407P; Aug. 12, 1982; 4 pages.

* cited by examiner

*Primary Examiner* — Mina Haghighatian
(74) *Attorney, Agent, or Firm* — Marshall, Gerstein & Borun LLP

(57) ABSTRACT

A container for liquid inhalation anesthetics, more particularly, an aluminum container that is suitable for storing halogenated inhalation anesthetics is described.

8 Claims, No Drawings

CONTAINER FOR INHALATION ANESTHETIC

RELATED APPLICATIONS

The present application claims priority on Provisional U.S. application Ser. No. 60/233,302, filed Sep. 15, 2000, which is incorporated herein by reference.

BACKGROUND OF THE INVENTION

The present invention relates to containers for liquid inhalation anesthetics, more particularly, to aluminum containers that are suitable for storing halogenated inhalation anesthetics.

Containers, such as those of the present invention, are used to store the liquid anesthetic agent, and to dispense it to a device for administering the agent to a patient. These devices are known in the art as "vaporizers', which mate with the container, receive the liquid anesthetic through an orifice in the container, vaporize the anesthetic, mix it with oxygen and optionally other gases, and mete out the gaseous mixture to the patient.

Inhalation anesthetics have traditionally been stored in glass containers. These containers, however, possess certain drawbacks. Glass requires careful handling to avoid breakage, and when breakage does occur, product is lost and injury may occur. In addition, it has been theorized that the inhalation anesthetic may react with components of the glass, leading to certain degradation products. C.f. U.S. Pat. No. 5,990,176.

A number of patents have taught the use of plastic containers for inhalation anesthetics and, in particular, sevoflurane. For example, U.S. Pat. No. 4,250,334 teaches the use of "Kel-F" plastic for a container for holding sevoflurane. "Kel-F" is understood to be the trade name for chlorotrifluoroethylene. U.S. Pat. No. 5,679,576 teaches the use of a container lined with PTFE, or polytetrafluoroethylene, for holding sevoflurane. U.S. Pat. No. 5,505,236, teaches the use of a plastic container with an inhalation anesthetic. While not specifically naming the inhalation anesthetic, it is believed that the commercial embodiment of the system shown in the '236 patent has been used with the anesthetic sevoflurane. Despite the existence of these patents teaching plastic containers to hold sevoflurane, a number of additional patents have recently issued that have taught the use of particular types of plastic for containers to hold sevoflurane. See, e.g., U.S. Pat. No. 6,074,668 (polyethylene napthalate), U.S. Pat. No. 6,083,514 (polymethylpentene) and U.S. Pat. No. 6,162,443 (polypropylene, polyethylene and ionomeric resins). The present invention presents an alternative type of container (aluminum) to hold sevoflurane.

In addition, containers for inhalation anesthetics made of certain plastics have been proposed. C.f. WO 99/34762, U.S. Pat. Nos. 6,074,668 and 6,162,443 and U.S. Patent Application Publication No. U.S. 2001/0000729 A1. While plastic containers are less likely to break than glass containers, they are still susceptible to breakage under common use conditions. Moreover, many plastics tend to be vapor permeable, allowing the inhalation anesthetic to escape the container and ambient vapors to enter the container over time, leading to possible contamination. Also, plastic containers are subject to deformation when exposed to elevated temperatures, which may be required during processing and treatment of the inhalation anesthetic-containing containers. Moreover, inhalation anesthetics have strong organic solvent properties, which typically will dissolve and/or react with the plastic material, leading to measurable impurities in the inhalation anesthetic.

Containers for sevoflurane have also been made of stainless steel. For example, U.S. Pat. No. 5,990,176 describes a container made of glass, plastic or stainless steel for holding sevoflurane. Metal containers have been used for various types of pharmaceutical products, as well as food and beverages. U.S. Pat. No. 6,008,273 describes an epoxy resin for coating the inside of a metal container for use as a food or beverage container.

SUMMARY OF THE INVENTION

The present invention overcomes the drawbacks of the prior art by providing a pharmaceutical product comprising a halogenated inhalation anesthetic stored within an aluminum container. It has been found that aluminum containers provide structural integrity, inertness and vapor-barrier properties that are well-suited for storage and handling of such inhalation anesthetics. In addition, aluminum is light in weight, resistant to heat-deformation, easily recycled and protects the inhalation anesthetic from light-induced degradation.

In further embodiments, the container is provided with an orifice for filling or removing the fluoroether-containing halogenated inhalation anesthetic, and a closure for the orifice. The closure preferably has a lining that helps the closure retain the desirable characteristics of the aluminum container. Alternatively, the closure may be provided with a valve assembly for regulating the flow of anesthetic. The closure may also be provided with indexing elements specially configured and unique to the particular inhalation anesthetic housed in the container to help ensure the anesthetic is administered only by the vaporizer for which it is designed.

The aluminum container may also be provided with a lining for added inertness. Typically, the container will be bottle-shaped.

DETAILED DESCRIPTION OF THE INVENTION

Halogenated inhalation anesthetics are well known and commercially available. These include sevoflurane (fluoromethyl-2,2,2-trifluoro/1/(tri-fluoromethyl)ethyl ether), desflurane (2-difluromethyl-1,2,2,2-tetrafluoroethyl ether), isoflurane (1-chloro-2,2,2-trifluoroethyl difluoromethyl ether), enflurane (2-chloro-1,1,2-trifluoroethyl difluoromethyl ether), methoxyflurane (2,2-dichloro-1,1-difluoroethyl methyl ether) and halothane (2-bromo-2-chloro-1,1,1-trifluoroethane), all of which are liquids at ambient conditions.

Aluminum containers suitable for use in the present invention are commercially available. Typically, they will be manufactured in the size and shape of the glass containers in which inhalation anesthetics are currently commercially sold. Commercially sold containers are bottle-shaped, i.e. they are outfitted with a neck whose mouth (orifice) can be sealed shut with a closure.

The aluminum containers of the present invention may be lined or unlined. Although the prior art hypothesizes that aluminum oxide present in glass containers may lead to degradation of the inhalation anesthetic, it has been found that no such degradation problem arises in the present invention. However, in some cases it may be desirable to provide the aluminum container with an inert lining to prevent the formation or release of flakes or small particles of aluminum during the manufacture of the container and formation of threads on the neck of the container. These flakes, while not a problem from a safety standpoint, may appear in the liquid anesthetic and be unpleasing from a cosmetic or visual standpoint.

Therefore, it is desirable to prevent formation of particles or flakes during the bottle manufacturing process.

Suitable lining materials are those which demonstrate no significant solubility in the inhalation anesthetic, i.e. do not render the inhalation anesthetic unusable. These lining materials include lacquers and enamels, and preferably contain an epoxyphenolic resin. Examples of lining materials that are commercially available include Type Nos. 7407P and 7940 HL/F from HOBA Industrie-Chemie GmbH, Bodelshausen, Germany. 7407P is a highly flexible liner suitable for aluminum containers having a thickness of 8-14 microns, and is based upon epoxyphenolic resin having a solid content of about 30 parts by weight, a delivered viscosity of about 90 sec. DIN 4 mm 20° C., a density of about 0.99 g/ml. The thickness of the liner may be less for certain applications.

The containers of the present invention will have an orifice for filling or removing the halogenated inhalation anesthetic, as well as a closure for the orifice. The closure should be chosen so as not to compromise the characteristics of the container, namely, it should provide structural integrity, inertness and vapor barrier properties. The closure will typically be a cap, such as those used on commercially available glass containers. The cap may be screw-on, snap-on or of a more elaborate design for fitting with commercially available vaporizers which are used to dispense the inhalation anesthetics. The closure may be made of aluminum or other metal, or of a polymer material. Particularly preferred are closures that are lined with the aforementioned lacquers, or with a polytetrafluoroethylene (PTFE). One such lining is commercially available under the name "Plytrax 100" and has a PTFE facing with a polyethylene foam backing, available from Norton Performance Plastics Corporation, 150 Day Road, Wayne N.J. 07470-4699, a subsidiary of Saint-Gobain Performance Plastics.

Alternatively, the closure may be provided with a valve assembly. As used herein, "valve assembly" means a closure provided with at least one valve for regulating flow of the anesthetic. Such closures are well known in the art, c.f. U.S. Pat. Nos. 5,505,236 and 5,617,906. These valve assemblies, serve to, alternately, close the orifice of the container to minimize loss of anesthetic from the container, and open the orifice by way of interaction with the vaporizer to deliver anesthetic to the vaporizer. Like caps, valve assemblies may be screwed or snapped onto the container.

In addition, these closures may be provided with indexing elements that allow the container to mate only with a vaporizer having corresponding indexing elements. This helps to ensure that an anesthetic is administered only through the vaporizer for which it was designed.

In a preferred embodiment, the container is bottle-shaped, whose neck (orifice) is sealed closed with a cap or valve assembly. The neck may be threaded, to allow screw-on of the cap or valve assembly. The valve assembly may be provided with indexing elements having a configuration that is unique and specific to the particular inhalation anesthetic stored in the container. The indexing elements help assure that the container storing a particular inhalation anesthetic will only mate to a vaporizer designed for that inhalation anesthetic. The container size and shape may be varied to indicate a particular type of inhalation anesthetic as well as to avoid mistaken mixing of different types of anesthetics in a vaporizer. Various alloys of aluminum may be used for the container, and still fall within the scope of the present invention. The container may be a bottle sized container for holding the final drug product, or may be in a larger tank or drum size for use during shipping, mixing or holding of the inhalation anesthetic in the bulk drug form or in a crude manufactured form awaiting final distillation. Also, the aluminum may be in the form of a liner or inner layer of another type of container, such as a plastic or steel container.

What is claimed is:

1. A pharmaceutical product comprising a container including a wall defining an interior chamber, said wall having an unlined aluminum inner surface and
    an inhalation anesthetic contained within said interior chamber, said inhalation anesthetic selected from the group consisting of sevoflurane, desflurane, isoflurane, enflurane, methoxyflurane and halothane.
2. The pharmaceutical product of claim 1 further comprising an orifice for filling or removing said inhalation anesthetic from the container and a closure for the orifice.
3. The pharmaceutical product of claim 2 wherein the closure comprises a cap.
4. The pharmaceutical product of claim 2 wherein the closure comprises a valve assembly for regulating flow of said inhalation anesthetic.
5. The pharmaceutical product of claim 2 wherein said closure is lined with a lacquer.
6. The pharmaceutical product of claim 2 wherein said closure is lined with a polymer.
7. The pharmaceutical product of claim 6 wherein said polymer is polytetrafluoroethylene (PTFE).
8. The pharmaceutical product of claim 2 wherein said closure includes indexing elements selected to correspond to indexing elements of a vaporizer.

* * * * *